United States Patent [19]

Tokura et al.

[11] Patent Number: 4,967,011
[45] Date of Patent: Oct. 30, 1990

[54] PROCESS FOR DECOMPOSING AROMATIC ACYLATED COMPOUND.HF-BF₃ COMPLEX

[75] Inventors: Nobuyuki Tokura; Tadayoshi Takefumi; Shunichi Matsumoto; Tatsuhiko Yanagawa; Yoshihiro Shiokawa; Ichiyo Ohtsuka, all of Kurashiki, Japan

[73] Assignee: Mitsubishi Gas Chemical Co., Inc., Tokyo, Japan

[21] Appl. No.: 392,514

[22] Filed: Aug. 11, 1989

[30] Foreign Application Priority Data

Sep. 30, 1988 [JP] Japan .................. 63-243919

[51] Int. Cl.$^5$ ............................. C07C 45/82
[52] U.S. Cl. ................... 568/325; 568/319; 568/322; 568/323
[58] Field of Search .............. 568/524, 319, 322, 323

[56] References Cited

U.S. PATENT DOCUMENTS

| | | | |
|---|---|---|---|
| 4,496,760 | 1/1985 | Devic | 562/460 |
| 4,663,485 | 5/1987 | Murphy et al. | 568/324 |
| 4,670,603 | 6/1987 | Piccolo et al. | 568/319 |

FOREIGN PATENT DOCUMENTS 0215351 3/1987 European Pat. Off. .
54-135756 10/1979 Japan .

*Primary Examiner*—James H. Reamer
*Attorney, Agent, or Firm*—Armstrong, Nikaido, Marmelstein, Kubovcik & Murray

[57] ABSTRACT

The present invention relates to a process for decomposing an aromatic acylated compound.HF-BF₃ complex in preparing an aromatic acylated compound by decomposing an aromatic acylated compound.HF-BF₃ complex obtained by reacting an aromatic compound with an acylating agent in the presence of HF-BF₃ as a catalyst, which comprises subjecting the aromatic acylated compound.HF-BF₃ complex to thermal decomposition in the presence of at least one aromatic hydrocarbon (A.H.) selected from benzene, toluene and chlorobenzene and at least one saturated aliphatic hydrocarbon (S.H.) selected from pentane, hexane and cyclohexane, as a decomposing agent.

5 Claims, 1 Drawing Sheet

4,967,011

PROCESS FOR DECOMPOSING AROMATIC ACYLATED COMPOUND·HF-BF₃ COMPLEX

BACKGROUND OF THE INVENTION

The present invention relates to a process for decomposing an aromatic acylated compound·$HF$-$BF_3$ complex in preparing an aromatic acylated compound by decomposing an aromatic acylated compound·$HF$-$BF_3$ complex obtained by reacting an aromatic compound with an acylating agent in the presence of $HF$-$BF_3$ used as a catalyst.

It is already known to obtain an aromatic acylated compound by reacting an aromatic compound with an acylating agent in the presence of $HF$-$BF_3$ as a catalyst. For example, Japanese Patent Application Kokai (Laid-open) No. 54-135756 discloses a method of obtaining a 2-alkyl-6-acylnaphthalene by reacting a 2-alkylnaphthalene with an acylating agent in the presence of $HF$ and $BF_3$. EP-A-0215351 discloses a method which comprises first converting an acid anhydride into an acyl fluoride in an acylating agent synthesis step, and then obtaining an aromatic acylated compound in the presence of $HF$ and $BF_3$ by using the isolated acylfluoride in an acylated compound synthesis step.

The reaction produced liquids obtained by these methods are each a $HF$ solution of an aromatic acylated compound·$HF$-$BF_3$ complex. On heating the liquid, the linkage between the aromatic acylated compound and $HF$-$BF_3$ is decomposed and $HF$ and $BF_3$ are recycled for use as catalyst.

For separation of the aromatic acylated compound and $HF$ and $BF_3$ from the reaction produced liquid, the following methods have hitherto been proposed:

(1) a method comprising heating the liquid at 20°–40° C. under reduced pressure to decompose the aromatic acylated compound·$HF$-$BF_3$ complex and distilling $HF$ and $BF_3$ away in the form of gas to effect separation, (2) a method comprising adding to the liquid a nitrogen compound such as ammonia, monoethylamine, piperidine, acetonitrile, nitroaniline, and chloroaniline to form a molecular compound, separating the molecular compound, and then heating it or reacting it with sulfuric acid, etc. to separate $HF$ and $BF_3$.

(3) a method comprising adding a decomposing agent inert to $HF$ and $BF_3$, e.g. aromatic hydrocarbons or halogenated aromatic hydrocarbons such as benzene, toluene and chlorobenzene (these aromatic hydrocarbons are hereinafter referred to as A.H.) and heating the mixture under reflux of the agent to effect decomposition.

The aromatic acylated compound in the reaction produced liquid obtained by reacting an aromatic compound with an acylating agent using $HF$-$BF_3$ as catalyst is susceptible to deterioration by heating, so that the above-mentioned operations need to be carried out as rapidly as possible. The prior methods for decomposing aromatic acylated compound·$HF$-$BF_3$ complex have the following difficulties.

(1) In the method of heating under reduced pressure, the degree of pressure reduction is determined according to the boiling point of acetylated compound. Aliphatic acylated compounds such as acetyl fluoride, propionyl fluoride and isobutyryl fluoride have relatively low boiling points, so that $HF$-$BF_3$ can be separated at temperatures of 20°–40° C. under low degree of pressure reduction. However, since aromatic acylated compounds have high boiling points, a considerably high degree of vacuum (namely, degree of pressure reduction) is necessary to distil the compounds at said temperature, which requires much power. Further, $HF$ and $BF_3$ are highly corrosive and can incur great danger if air leaks into the apparatus under high vacuum. Therefore, this method is difficult to practice on commercial scale.

(2) The method comprising adding nitrogen compounds to form molecular compounds and then decomposing the latter compounds newly requires operations of separating the molecular compounds. Accordingly, the catalyst recovery step becomes very complicated and the method is not suited to practical use.

(3) In the method of using inert decomposing agents, usually a decomposition-distillation column provided with a heater at the column bottom is used to effect the separation of catalyst as rapidly as possible. The inert agents used are the above-mentioned A.H. The aromatic acylated compound·$HF$ $BF_3$ complex is rapidly decomposed by contact with the A.H. vapor and is distilled, while $HF$ and $BF_3$ are separated from the column top. However, a part of A.H. is entrained with $HF$ and $BF_3$ and is distilled out from the column top along with $HF$ and $BF_3$. $HF$ and $BF_3$ are cooled in a condenser together with A.H. vapor, $HF$ and A.H. are condensed, and $BF_3$ is separated as non-condensable gas. The condensate is separated in a separator into $HF$ and A.H.. The separated $HF$ contains A.H. associated with the non-condensable gas ($BF_3$), dissolved therein. When the concentration of A.H. in $HF$ is high, alkylated products and acylated products of said A.H. are formed by side reactions in the acylating agent synthesis step using recovered $HF$, resulting in decrease in yields in the acylating agent synthesis step and in the synthesis step of intended acylated compounds. Further, since the alkylated products of A.H., e.g. tetraisopropylbenzene, is insoluble in $HF$, they can cause blockages of piping, etc. Thus, the A.H. becomes an obstacle to the recycling of $HF$ and $BF_3$ of the catalyst. Although there is further known, to separate A.H. dissolved in $HF$, a method comprising subjecting the $HF$ solution after separation of non-condensable gas ($BF_3$) to redistillation, this method requires a separate distillation column which requires a considerably large number of stages and reflux ratio. Therefore, the construction cost becomes high and energy consumption for redistillation is large.

SUMMARY OF THE INVENTION

The present inventors have made extensive studies on the process for decomposing aromatic acylated compound·$HF$-$BF_3$ complexes, which has had difficulties as described above. As the result, it has been found that when the $HF$-$BF_3$ complex is distilled by using, as a decomposing agent, a liquid mixture of said A.H. with at least one saturated hydrocarbons selected from pentane, hexane and cyclohexane, which has a lower boiling point than that of A.H., (these saturated hydrocarbons being hereinafter referred to as S.H.), the A.H. concentration in the decomposing agent at the column top decreases markedly and the A.H. concentration in recovered $HF$ also decreases and that resultant side reactions in the acylating agent synthesis step which uses recovered $HF$ and in the acylated compound synthesis step are suppressed, the yields of the acylating agent and acylated compound are improved, and recycling of catalyst is facilitated, and thus attained the present invention.

Thus, according to the present invention, there is provided a process for decomposing an aromatic acylated compound·HF-BF$_3$ complex in preparing an aromatic acylated compound by decomposing an aromatic acylated compound·HF-BF$_3$ complex obtained by reacting an aromatic compound with an acylating agent in the presence of HF-BF$_3$ as a catalyst, which comprises subjecting the aromatic acylated compound·HF-BF$_3$ complex to thermal decomposition in the presence of at least one aromatic hydrocarbon (A.H.) selected from benzene, toluene and chlorobenzene and at least one saturated aliphatic hydrocarbon (S.H.) selected from pentane, hexane and cyclohexane, as a decomposing agent.

DETAILED DESCRIPTION OF THE INVENTION

Figure 1:
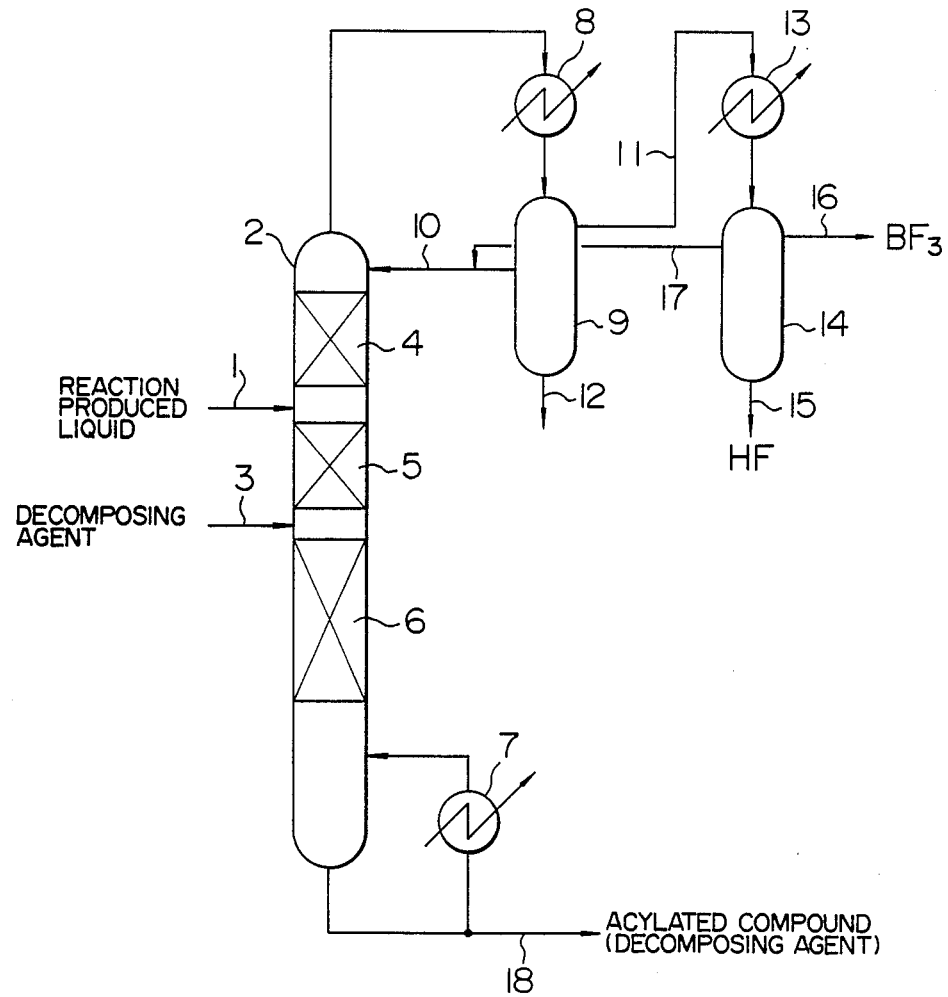
FIG. 1 shows an example of a decomposition-distillation column used in the present invention for decomposing an aromatic acylated compound·HF-BF$_3$ complex and separating the aromatic acylated compound from HF-BF$_3$.

The aromatic compounds used for obtaining the acylated compounds according to the present invention include, for example, alkylbenzenes such as toluene, xylene, cumene, and butylbenzene, naphthalene, alkyl naphthalenes such as methylnaphthalene and the like, phenols and naphthols, and aromatic ethers such as anisol and phenyl ether.

The acylating agents include, for example, acyl fluoride such as acetyl fluoride, propionyl fluoride, isobutyryl fluoride, ethylmethylacetyl fluoride, and benzoyl fluoride, carboxylic acids such as acetic acid, propionic acid and butyric acid and the esters thereof, and acid anhydrides such as acetic anhydride, propionic anhydride, and butyric anhydride.

The amount of the acylating agent to be used is 1.3 or less, preferably 0.8–1.0, in terms of molar ratio relative to the starting aromatic compound. When the acylating agent is in excess, the agent will remain in the reaction produced liquid and exert an undesirable influence at the time of catalyst separation.

The amount of HF to be used is 5 times by mole or more, preferably 10–15 times by mole, to the amount of acylating agent. BF$_3$ is preferably used in an equivalent amount to the acylating agent or in slight excess.

The temperature of acylation is $-20° \sim +30°$ C., preferably $-10° \sim +20°$ C. Elevating the temperature results in increase in reaction velocity but also in increase in side-reaction velocity. The reaction temperature should be determined also in consideration of the melting points of raw materials.

The reaction is carried out, under usual conditions, at a slightly applied pressure of from normal pressure to 5 kg/cm$^2$ G. The pressure is determined according to the molar ratio of the catalyst used and the reaction temperature.

Since the reaction proceeds in a homogeneous liquid phase, it requires no vigorous stirring.

The reaction produced liquid thus obtained is a HF solution of an aromatic acylated compound·HF-BF$_3$ complex, HF-BF$_3$ is decomposed from the complex by heating, and HF and BF$_3$ can be vaporized and separated.

The catalyst separation needs to be operated as rapidly as possible to avoid thermal deterioration of the reaction product. Although it is already known that using A.H. as a decomposing agent inert to HF-BF$_3$ is effective for thermal decomposition of the complex to proceed smoothly, it has been further found that the use of a liquid mixture of A.H. and S.H. lowers the concentration of A.H. in the decomposing agent accompanying HF-BF$_3$, and hence is advantageous in operations of catalyst recycling.

As to the mixing proportion of A.H. and S.H., the amount of S.H. is 0.1–0.8 times by weight, preferably 0.2–0.5 times by weight, relative to A.H. When the proportion of S.H. to A.H. is too small, the amount of A.H. associated with HF and BF$_3$ increases, which results in such difficulties as causing decrease in yields and blockages of piping in the acylating agent synthesis step and the acylated compound synthesis step. On the other hand, when the proportion of S.H. to A.H. is too large, the solubility of the aromatic acylated compound in the decomposing agent decreases, resulting in deposition of the acylated compounds in the distillation column, packed column, or piping and leading to the risk of blocking.

The amount of the decomposing agent to be used is 0.2–1.5 times by weight, preferably 0.5–1.0 times by weight, relative to the amount of reaction liquid. When the amount of the decomposing agent used is too large, energy consumption necessary for heating increases. When the amount is too small, it results in a risk of causing blockages in pipelines etc. since the solubility of the acylated compound is decreased.

An example of apparatuses used for decomposition of an aromatic acylated compound·HF-BF$_3$ complex using a liquid mixture of A.H. and S.H. and separation of the aromatic acylated compound from HF and BF$_3$ is a distillation apparatus as shown in FIG. 1. In FIG. 1, the reaction produced liquid is introduced through a passage 1 into a distillation column 2. A liquid mixture of A.H. and S.H., the decomposing agent, is introduced through a passage 3. A packed column or a plate column is used for the distillation column 2. To increase the efficiency of separation of HF and BF$_3$ from the aromatic acylated compound, the packed column, when it is used, is divided into an upper packed part 4, middle packed part 5 and lower packed part 6, and the reaction produced liquid is supplied between the upper packed part 4 and the middle packed part 5, and the decomposing agent between the middle packed part 5 and the lower packed part 6.

Heating at a reboiler 7 yields the vapor of HF, BF$_3$ and the decomposing agent from the top of the distillation column. In a primary condenser 8, mainly a part of the decomposing agent and an azeotropic composition of three components, namely HF, BF$_3$ and water, are condensed. In a primary separator 9, the decomposing agent and the azeotropic composition separate into two layers owing to density difference. The decomposing agent is withdrawn through a passage 10 and refluxed to the distillation column. The azeotropic composition containing HF, BF$_3$ and water is withdrawn through a passage 12. From a passage 11, are separated the vapors of HF and BF$_3$ and of the decomposing agent containing a low concentration of A.H., and further condensed in a secondary condenser 13. From a secondary separator 14, BF$_3$ vapor is recovered through a passage 16 and, as to the condensed decomposing agent and HF, HF is recovered through a passage 15 based on the difference in density, and the decomposing agent is refluxed through a passage 17 to the distillation column. At the column bottom, a liquid containing the aromatic acylated compound and the decomposing agent is obtained through a passage 18. The liquid is sent to the purification step of the aromatic acylated compound, where the decomposing agent is separated and recycled to the distillation column.

The catalyst separation described above is favorably operated under normal or slightly applied pressure from the viewpoint of process advantage. It requires heating at 100°–180° C. at the column bottom.

DESCRIPTION OF THE PREFERRED EMBODIMENT(S)

The present invention will be described further in detail below with reference to Examples. However, the invention is in no way limited by the Examples.

EXAMPLE 1

In FIG. 1, a distillation column 55 mm in inner diameter and 1,300 mm in hight was packed with ½B Raschig rings, the upper packed part being filled in a depth of 0.3 m, the middle packed part in a depth of 0.3 m, and the lower packed part in a depth of 0.4 m, and a HF-$BF_3$ complex was decomposed therein.

The reaction liquid fed to the distillation column contained about 16% by weight of 2-isobutyryl-6-methylnaphthalene (hereinafter abbreviated as BMN) obtained by acylation of 2-methylnaphthalene using isobutyryl fluoride as an acylating agent. The liquid feed rate was 2855 g/hr. The decomposing agent used was a liquid mixture of benzene (Bz) and hexane (Hx) of a weight ratio of 80:20. The amount and the composition of the reaction produced liquid, operation conditions for the distillation column, etc. are shown in Table 1. The concentration of benzene in HF recovered from the column top was found to be 2.2% by weight.

EXAMPLE 2

An experiment was conducted in the same manner as in Example 1 except that a reaction produced liquid containing about 20% by weight of BMN was fed at a rate of 4000 kg/hr. The amount and the composition of the reaction produced liquid, operation conditions for the distillation column, etc. are shown in Table 1. The concentration of benzene in HF recovered from the column top was found to be 2.0% by weight.

EXAMPLE 3

An experiment was conducted in the same manner as in Example 1 except that a liquid mixture of benzene and hexane in a weight ratio of 70:30 was used as a decomposing agent and a reaction liquid containing about 21% by weight of BMN was fed at a rate of 3653 kg/hr. The amount and the composition of the reaction produced liquid, operation conditions for the distillation column, etc. are shown in Table 1. The concentration of benzene in HF recovered from the column top was found to be 0.3% by weight.

EXAMPLE 4

An experiment was conducted in the same manner as in Example 3 except that a reaction produced liquid containing about 25% by weight of BMN was fed at a rate of 3342 kg/hr. The amount and the composition of the reaction produced liquid, operation conditions for the distillation column, etc. are shown in Table 1. The concentration of benzene in HF recovered from the column top was found to be 0.9% by weight.

EXAMPLE 5

An experiment was conducted in the same manner as in Example 1 except that a reaction produced liquid containing about 29% by weight of 1-isobutyryl-2,4-dimethylbenzene (hereinafter abbreviated as BDMB) obtained by acylation of m-xylene using isobutyl fluoride as an acylating agent was fed at a rate of 1776 g/hr. The amount and the composition of the reaction produced liquid, operation conditions for the distillation column, etc. are shown in Table 1. The concentration of benzene in HF recovered from the column top was found to be 2.1% by weight.

EXAMPLE 6

The procedures in Example 1 were repeated except that a reaction produced liquid containing about 29% by weight of 2,4′-dimethyl-butyrophenone (hereinafter abbreviated as DMBP) obtained by acylation of toluene using ethylmethylacetyl fluoride as an acylating agent was fed at a rate of 2,200 g/hr. The amount and the composition of the reaction produced liquid, operating conditions for the distillation column, etc. are shown in Table 1. The concentration of benzene in HF recovered from the column top was found to be 2.0% by weight.

EXAMPLE 7

The procedures in Example 1 were repeated except that a liquid mixture of toluene (T1) and hexane was used as a decomposing agent and a reaction produced liquid containing about 32% of BMN was fed at a rate of 2600 g/hr. The amount and the composition of the reaction liquid, operation conditions for the distillation column, etc. are shown in Table 1. The concentration of toluene in HF recovered from the column top was found to be 1.8% by weight.

TABLE 1

| Example No. | | 1 | 2 | 3 | 4 | 5 | 6 | 7 | 8 | 9 | Comp. 1 | Comp. 2 |
|---|---|---|---|---|---|---|---|---|---|---|---|---|
| Acylated compound | | BMN | BMN | BMN | BMN | BDMB | DMBP | BMN | BMN | BMN | BMN | BMN |
| Feed rate of reaction produced liquid | | 2855 g/H | 4000 | 3653 | 3342 | 1776 | 2200 | 2600 | 4300 | 2900 | 2085 | 3600 |
| Break- down | HF | 1600 | 1750 | 1900 | 1470 | 670 | 907 | 1100 | 1700 | 1450 | 1005 | 1850 |
| | BF3 | 450 | 796 | 366 | 539 | 446 | 487 | 503 | 881 | 519 | 335 | 660 |
| | Acylated compound | 456 | 782 | 759 | 829 | 517 | 628 | 831 | 1415 | 767 | 560 | 961 |
| | Unreacted material | 235 | 369 | 389 | 322 | 63 | 25 | 66 | 169 | 74 | 92 | 13 |
| | Others | 114 | 303 | 239 | 182 | 80 | 153 | 100 | 135 | 90 | 93 | 116 |
| Decomposing agent | | Bz/Hx | Bz/Hx | Bz/Hx | Bz/Hx | Bz/Hx | Bz/Hx | T1/Hx | T1/Hx | CB/CH | Bz | T1 |
| Mixing ratio | | 80:20 | 80:20 | 70:30 | 70:30 | 80:20 | 80:20 | 80:20 | 80:20 | 70:30 | 100 | 100 |
| Feed rate | | 1420 g/H | 1336 | 1220 | 1545 | 650 | 650 | 1402 | 1402 | 1818 | 1405 | 1560 |
| Decomposition operation | | | | | | | | | | | | |

TABLE 1-continued

| Example No. | 1 | 2 | 3 | 4 | 5 | 6 | 7 | 8 | 9 | Comp. 1 | Comp. 2 |
|---|---|---|---|---|---|---|---|---|---|---|---|
| Acylated compound | BMN | BMN | BMN | BMN | BDMB | DMBP | BMN | BMN | BMN | BMN | BMN |
| Feed rate of reaction produced liquid | 2855 g/H | 4000 | 3653 | 3342 | 1776 | 2200 | 2600 | 4300 | 2900 | 2085 | 3600 |
| conditions | | | | | | | | | | | |
| Pressure | 4.0 K/G | 4.0 | 4.0 | 4.0 | 4.0 | 4.0 | 4.0 | 4.0 | 2.0 | 4.0 | 4.0 |
| Temperature | 150° C. | 158 | 156 | 155 | 158 | 158 | 170 | 165 | 165 | 155 | 173 |
| Overhead withdrawal rate | | | | | | | | | | | |
| $BF_3$ | 444 g/H | 788 | 344 | 513 | 444 | 450 | 495 | 859 | 503 | 329 | 652 |
| HF | 1592 | 1732 | 1890 | 1465 | 666 | 899 | 1056 | 1666 | 1431 | 996 | 1806 |
| Decomposing agent | 100 | 120 | 24 | 43 | 50 | 117 | 160 | 198 | 70 | 59 | 60 |
| A.H. concentration in HF | 2.2 wt % | 2.0 | 0.3 | 0.9 | 2.1 | 2.0 | 1.8 | 1.6 | 1.5 | 5.9 | 4.7 |
| Bottom withdrawal rate | | | | | | | | | | | |
| Acylated compound | 449 g/H | 762 | 744 | 817 | 509 | 575 | 814 | 1394 | 744 | 550 | 894 |
| Decomposing agent | 1320 | 1216 | 1196 | 1502 | 600 | 533 | 1242 | 1204 | 1748 | 1346 | 1500 |
| Unreacted material | 122 | 228 | 265 | 183 | 15 | 5 | 26 | 126 | 17 | 60 | 20 |
| Others | 248 | 490 | 467 | 364 | 142 | 271 | 209 | 255 | 205 | 150 | 228 |

EXAMPLE 8

The procedures in Example 1 were repeated except that a liquid mixture of toluene and pentane ($P_n$) was used as a decomposing agent and a reaction liquid containing about 33% by weight of BMN was fed at a rate of 4300 g/hr. The amount and the composition of the reaction produced liquid, operation conditions for the distillation column, etc. are shown in Table 1. The concentration of toluene in HF recovered from the column top was found to be 1.6% by weight.

EXAMPLE 9

The procedures in Example 1 were repeated except that a liquid mixture of chlorobenzene (CB) and cyclohexane (CH) was used as a decomposing agent and a reaction produced liquid containing about 26% by weight of BMN was fed at a rate of 2900 g/hr. The amount and the composition of the reaction produced liquid, operation conditions for the distillation column, etc. are shown in Table 1. The concentration of chlorobenzene in HF recovered from the column top was found to be 1.5% by weight.

COMPARATIVE EXAMPLE 1

The procedures in Example 1 were repeated except that benzene alone was used as a decomposing agent in place of the liquid mixture of benzene and hexane, and a reaction produced liquid containing about 27% by weight of BMN was fed at a rate of 2085 g/hr. The amount and the composition of the reaction liquid, operation conditions for the distillation column, etc. are shown in Table 1. The concentration of benzene in HF recovered from the column top was found to be 5.9% by weight.

COMPARATIVE EXAMPLE 2

The procedures in Example 1 were repeated except that toluene alone was used as a decomposing agent and a reaction liquid containing about 27% by weight of BMN was fed at a rate of 3600 g/hr. The amount and the composition of the reaction produced liquid, operation conditions for the distillation column, etc. are shown in Table 1. The concentration of toluene in HF recovered from the column top was found to be 4.7% by weight.

EFFECT OF THE INVENTION

As shown in respective Examples, when a liquid mixture of A.H. and S.H. is used as a decomposing agent, the amount of A.H. contained in recovered HF and $BF_3$ as catalyst has advantages in that aromatic compounds can be easily acylated by simple operations and at low pressure and that HF-$BF_3$ can be recycled for use as catalyst. According to the present invention, the acylation process is further improved and the yields in the acylating agent synthesis step and the acylated compound synthesis step are improved. Thus, the present invention is of great industrial importance.

What is claimed is:

1. A process for decomposing an aromatic acylated compound·HF-$BF_3$ complex obtained by reacting an aromatic compound selected from the group consisting of alkylbenzene, naphthalene, alkylnaphthalene, phenol and aromatic ethers, with an acylating agent in the presence of HF-$BF_3$ as a catalyst, comprising subjecting the aromatic acylated compound·HF-$BF_3$ complex to thermal decomposition in a distillation column heated to 100°-180° C. at the column bottom in the presence of, as a decomposing agent, at least one aromatic hydrocarbon selected from benzene, toluene and chlorobenzene and at least one saturated aliphatic hydrocarbon selected from pentane, hexane and cyclohexane.

2. A process for decomposing an aromatic acylated compound·HF-$BF_3$ complex obtained by reacting an aromatic compound selected from the group consisting of alkylbenzene, naphthalene, alkylnaphthalene, phenol, and aromatic ethers with an acylating agent in the presence of HF-$BF_3$ as a catalyst, comprising the steps of:

(a) feeding the aromatic acylated compound·HF-$BF_3$ complex to a distillation column heated at 100°-180° C. at the column bottom;

(b) subjecting the aromatic acylated compound·HF-$BF_3$ complex to thermal decomposition in the presence of as a decomposing agent, at least one aromatic hydrocarbon selected from the group consisting of benzene, toluene and chlorobenzene and at least one saturated aliphatic hydrocarbon selected from the group consisting of pentane, hexane and cyclohexane; and (c) withdrawing HF and $BF_3$ from the column top and the aromatic acylated compound and the decomposing agent from the column bottom.

3. A process according to claim 1 wherein the acylating agent is any one of acyl fluorides, carboxylic acids and the esters thereof, and acid anhydrides.

4. A process according to claim 1 wherein the amount of saturated aliphatic hydrocarbon is 0.1-0.8 times by weight relative to that of aromatic hydrocarbon.

5. A process according to claim 1 wherein the decomposing agent is used in an amount of 0.2-1.5 times by weight relative to the amount of reaction liquid formed by acylation.

* * * * *